United States Patent
Kelly et al.

(10) Patent No.: US 11,579,137 B2
(45) Date of Patent: Feb. 14, 2023

(54) SYSTEM AND METHOD FOR FIBROGRAM FIBER QUALITY EVALUATION

(71) Applicant: TEXAS TECH UNIVERSITY SYSTEM, Lubbock, TX (US)

(72) Inventors: Brendan Kelly, Lubbock, TX (US); Eric Hequet, Lubbock, TX (US); Md Abu Sayeed, Lubbock, TX (US); Zach Hinds, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 353 days.

(21) Appl. No.: 16/763,924

(22) PCT Filed: Nov. 13, 2018

(86) PCT No.: PCT/US2018/060779
§ 371 (c)(1),
(2) Date: May 13, 2020

(87) PCT Pub. No.: WO2019/094946
PCT Pub. Date: May 16, 2019

(65) Prior Publication Data
US 2020/0363391 A1    Nov. 19, 2020

Related U.S. Application Data

(60) Provisional application No. 62/585,206, filed on Nov. 13, 2017.

(51) Int. Cl.
*G01N 33/36* (2006.01)
*D01H 13/32* (2006.01)

(52) U.S. Cl.
CPC .......... *G01N 33/362* (2013.01); *D01H 13/32* (2013.01)

(58) Field of Classification Search
CPC ....... D01G 99/00; G01N 33/362; D01H 13/32
See application file for complete search history.

(56) References Cited

U.S. PATENT DOCUMENTS

2002/0157164 A1* 10/2002 Shofner ............... G01N 33/365
2/66
2003/0059090 A1* 3/2003 Zhang ................. G01N 33/362
382/110

(Continued)

FOREIGN PATENT DOCUMENTS

WO      2019094946 A1    5/2019

OTHER PUBLICATIONS

Chaterrjee, P., et al., "Development of a meta-model for the determination of technological value of cotton fiber using design of experiments and the TOPSIS method", Journal of Natural Fibers, vol. 15, No. 6, Nov. 2, 2018, pp. 882-895. 16 pages.

(Continued)

*Primary Examiner* — Sang H Nguyen
(74) *Attorney, Agent, or Firm* — Dickinson Wright PLLC; Kristopher Lance Anderson (57) ABSTRACT

Disclosed is a system and method for extraction of information of within sample distribution of fiber quality from high-volume instrument (HVI) fibrogram to better predict yarn quality than the standard HVI output. The present invention allows for information on fiber quality to be obtained while avoiding testing samples with more expensive techniques. The disclosed system and method extracts HVI data for collecting a respective set of initial fibrograms from a set of fiber samples and representing them as a distance matrix to form a matrix of transformed fibrogram data, said matrix of transformed fibrogram data comprising a vector of scores to represent each sample and thereafter explaining variation in yarn quality by extracting all of the information available from the fibrogram.

21 Claims, 11 Drawing Sheets

(56) References Cited

U.S. PATENT DOCUMENTS

| | | | | |
|---|---|---|---|---|
| 2004/0141188 | A1* | 7/2004 | Rust | G01N 33/362 356/429 |
| 2007/0291270 | A1* | 12/2007 | Shofner | G01B 11/02 356/429 |
| 2009/0037139 | A1* | 2/2009 | Rust | G01B 11/024 702/158 |
| 2013/0252289 | A1* | 9/2013 | Strobel | C10L 1/18 435/166 |
| 2014/0162274 | A1* | 6/2014 | Kunin | C12Q 1/689 435/252.4 |

OTHER PUBLICATIONS

Kelly, B., "Multivariate analysis of fiber properties and their relation to yarn properties", Ph. D Thesis, Dec. 2014, Texas Tech University, Lubbock, TX, pp. vii-viii and 157-181. 28 pages.

Kelly, B., et al., "Variation in the advanced fiber information system cotton fiber length-by-number distribution captured by high vol. instrument fiber length parameters", Textile Research Journal, vol. 88, No. 7, Feb. 1, 2017, pp. 754-765. 12 pages.

Majumdar, A., et al., "A new approach to determine the quality value of cotton fibres using multi-criteria decision making and genetic algorithm", Fibers and Polymers, vol. 15, No. 12, Dec. 1, 2014, pp. 2658-2664. 8 pages.

Majumdar, A., et al., "Determination of quality value of cotton fibre using hybrid AHP-TOPSIS method of multi-criteria decision-making", Journal of the Textile Institute, vol. 96, No. 5, 2005, pp. 303-309. 8 pages.

Zeng, L., et al., "Correlated selection responses of fiber properties measured by high volume instrument and advanced fiber information system in Upland cotton", Euphyti CA, vol. 213, 278, Nov. 17, 2017, pp. 1-10.

International Bureau, International Preliminary Report on Patentability for PCT/US2018/060779 dated May 28, 2020, 10 pages.

International Searching Authority, International Search Report and Written Opinion for PCT/US2018/060779 dated Apr. 15, 2019, 18 pages.

* cited by examiner

SYSTEM AND METHOD FOR FIBROGRAM FIBER QUALITY EVALUATION

CROSS-REFERENCE TO RELATED APPLICATIONS

The present application is the 35 U.S.C. § 371 national application of International Application Number PCT/US18/60779, entitled "System And Method For Fibrogram Fiber Quality Evaluation," filed on Nov. 13, 2018, which claims priority to U.S. Provisional Patent Application 62/585,206 filed on Nov. 13, 2017, titled "System and Method for Fibrogram Fiber Quality Evaluation". These applications are hereby incorporated herein by reference in their entirety for all purposes.

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

TECHNICAL FIELD

The present invention relates in general to the field of fiber quality measurement. In particular, the present invention provides for utilization of a full fibrogram for quantification of various fiber qualities. The disclosed systems and methods support a wide variety of scenarios and include various products and services,

STATEMENT OF FEDERALLY FUNDED RESEARCH

None.

BACKGROUND OF THE DISCLOSURE

In the textile industry, fibers need to be tested for different qualities including length, strength, fineness, and color in order to determine where they would be the most useful. The U.S. textile industry consumes around 718,490 metric tons of cotton per year. Also, about 80% of the U.S. cotton crop is now exported to surrounding countries. The quality and types of fibers that come from cotton are numerous. Cotton fiber with certain quality characteristics are more suitable for certain applications, and the wrong quality of fiber could lead to bad quality products being produced, There are different types of machines that are able to assess the quality of fibers, with the most common being the high volume instrument (HVI). HVI systems take parallel bundles of fibers and report on the mean length and uniformity index of the bundle. However, there is very little data reported concerning individual fiber metrics of the distribution of fiber lengths. Without these added fiber qualities, the ability to accurately predict yarn quality becomes much harder. One way around this lack of information is to use a different method of fiber analysis known as Advanced Fiber information System (AFIS). AFIS is able to provide a more detailed report about individual fiber qualities; however, AFIS testing is costly, takes more time, and is not as widely distributed as HVI, New cotton germplasm is needed that is capable of producing cotton fiber with a within sample distribution of fiber length competitive on demanding international spinning markets. Current methods of measuring the within sample distribution, the Advanced Fiber Information System (AFIS), are too slow and expensive for widespread implementation in germplasm development. The High Volume Instrument (HVI) provides Upper Half Mean Length (UHML) and Uniformity Index (UI), and is in widespread use in many breeding programs. However, HVI length parameters do not capture enough information about the within sample distribution of fiber length. These HVI length parameters provide only a portion of the information about fiber length measured by the instrument.

It is therefore a need in the art to develop an economically feasible system for assessing fibrogram information within a sample of fiber,

SUMMARY OF THE DISCLOSURE

The present invention addresses failings in the art by providing a system and method to extract more information about the within sample distribution of fiber quality from the HVI fibrogram (The part of the HVI measuring fiber length). The additional information provided by the fibrogram contains important information about variation in fiber length that impacts yarn quality. These results are demonstrated on two sets of bales, a set of 72 samples produced from 12 commercial varieties grown at 6 locations across the high plains, and a set of 126 breeder samples exhibiting diverse variation in fiber quality.

It is therefore an object of the present invention to provide a system for estimating unknown fiber quality of a fiber sample, comprising: an high volume instrument (HVI) for collecting a respective set of initial fibrograms from a set of fiber samples from the HVI and representing them as a distance matrix; and a computer for: decomposing the total variation captured in said matrix form from the distance matrix to form a matrix of transformed fibrogram data, said matrix of transformed fibrogram data comprising a vector of scores to represent each sample; mutually exclusively partitioning the total multivariate space captured by the initial fibrograms into a set of independent variables from the HVI; and explaining variation in yarn quality by regressing each yarn quality parameter over the vector of scores obtained from the matrix of transformed fibrogram data.

It is another object of the present invention to provide a method of estimating unknown fiber quality of a fiber sample, comprising: collecting a respective set of initial fibrograms from a set of fiber samples from a high volume instrument (HVI) and representing them as a distance matrix; decomposing the total variation captured in said matrix form from the distance matrix to form a matrix of transformed fibrogram data, said subsequent matrix of transformed fibrogram data comprising a vector of scores to represent each sample; mutually exclusively partitioning the total multivariate space captured by the initial fibrograms into a set of independent variables from the HVI; and explaining variation in yam quality by regressing each yarn quality parameter over the vector of scores obtained from the transformed fibrogram data.

The present invention therefore provides useful information to many, sectors of the cotton industry. Breeders may utilize the information provided by present invention to evaluate the within-sample distribution of fiber length produced by their germplasm. The within-sample distribution of fiber length is an important attribute of fiber quality because it impacts processing performance and yarn quality. Current methods used for evaluating the within-sample distribution of fiber length, the AFIS, are much to slow and expensive for use in germplasm evaluation, Researchers may use information provided by the present invention to see how agronomic treatments may impact the length distribution. The present invention provides processors a better indication of future processing performance and yarn quality compared with current HVI length parameters, as the current length parameters are limited in what type of length variation they characterize. Spinning mills blend bales to ensure processing performance and end product quality. Mills could use information provided by this invention to better manage these blends and manage equipment settings for optimal performance. Excessive within-sample variation in fiber length can be a problem in some types of spinning systems, such as airjet spinning. Traditional length parameters provided by the HVI do not suitably characterize within sample variation in fiber length, and do not provide a good indication of potential performance in spinning systems depending on a suitable within-sample distribution of fiber length. The present invention therefore presents this additional information oat fiber length needed for evaluating bales for potential use in these systems.

In one aspect, the distance matrix is based on the Euclidean distance metric between initial fibrograms. In another aspect the distance matrix is based on the chi-squared distance metric between initial fibrograms. In yet another aspect the distance matrix is based on the Bray-Curtis dissimilarity metric between initial fibrograms. In another aspect the distance matrix is based on a correlation matrix between initial fibrograms.

In one aspect of the present invention, the decomposition may comprise singular value decomposition. The vector of scores may further comprise at least one score representing the largest source of total variation among all initial fibrograms. The vector of scores may further comprise at least two scores representing a first score representing the largest source of total variation among all initial fibrograms, and a second score representing the second largest source of total variation among all initial fibrograms. In another aspect the vector of scores further comprises more than two scores representing ranked scores representing the source of total variation among all initial fibrograms from largest to smallest.

The fiber quality further may comprise quality parameters selected various known and accepted parameters of importance to fiber quality, including but not limited to: breaking force, work-to-break, elongation at break, yarn irregularity (CVm %), thin places, thick places, peps, hairiness, imperfection index, and combinations thereof.

The details of one or more embodiments of the present invention are set forth in the accompanying drawings and description below. Other aspects, features and advantages will be apparent from the description and drawings.

BRIEF DESCRIPTION OF THE DRAWINGS

The foregoing and other objects, features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure.

DETAILED DESCRIPTION OF THE DISCLOSURE

While the making and using of various embodiments of the present invention are discussed in detail below, it should be appreciated that the present invention provides many applicable inventive concepts that can be embodied in a wide variety of specific contexts, goods, or services. The specific embodiments discussed herein are merely illustrative of specific ways to make and use the disclosure and do not delimit the scope of the disclosure.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The present invention will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, compositions, or systems. Accordingly, embodiments may, for example, take the form of methods, compositions, compounds, materials, or any combination thereof. The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or, "and/or," as used herein may include a variety of meanings that may depend at least in part upon the context art which such terms are used. Typically, "of" if used to associate a list, such as B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending, at least in part on context.

After a period of rapid expansion from 1980 to 1997, the U.S. textile industry began a phase of rapid decline, At its peak (1997), the U.S. textile manufacturing industry consumed 2,471,000 metric tons of cotton (about 10.8 million bales). At its lowest point, in 2011, the consumption of cotton in the U.S. shrunk to 718,490 metric tons (about 3.3 million bales). Since 2008, the consumption has oscillated between 3.3 and 3.8 million bales per year. The decreased consumption of cotton within the U.S. textile manufacturing industry led to an increased reliance on the international market fix the sale of U.S. cotton. For example, about 80% of the U.S. cotton crop is now exported.

This process, in turn, is transforming the requirements on fiber properties. The spinning industry needs cotton fiber with an improved within sample distribution of fiber length to meet production goals. Indeed, within sample variation in cotton fiber length can prohibit the use of cotton fiber as a raw material in mills that use newer spinning technologies, such as airjet. In order to market cotton bales to spinning mills, the quality of every bale of cotton produced in the United States is assessed on a High Volume Instrument (HVI). The HVI is also the most common method for measuring fiber quality in research, such as breeding. However, current HVI fiber quality measurement protocols are unable to capture the within sample variation in fiber length needed to explain processing performance and potential yarn quality. This technology enables the industry to access information about the within sample distribution of fiber length from the most commonly used method for evaluating fiber length, the fibrograph.

The U.S. industry has long been focused on the production of medium and coarse yarns and has long emphasized open end rotor spinning, rather than ring spinning. But the focus of the dominant international textile industries is on the finer yarns and ring spinning. Thus textile mills interested in sourcing cotton from the global market emphasize those cotton growths with fiber profiles adapted to this market (fibers that are long, uniform, mature, fine, strong, and with low contamination levels). At the same time, increasing labor costs in Asia where most of the cotton spinning industry is located, are forcing spinning mills to consider potential alternative spinning technologies such as airjet spinning. Airjet spinning is not cotton friendly. Natural sample variation in cotton fiber length restricts its use as a raw material in airjet mills.

Figure 1:
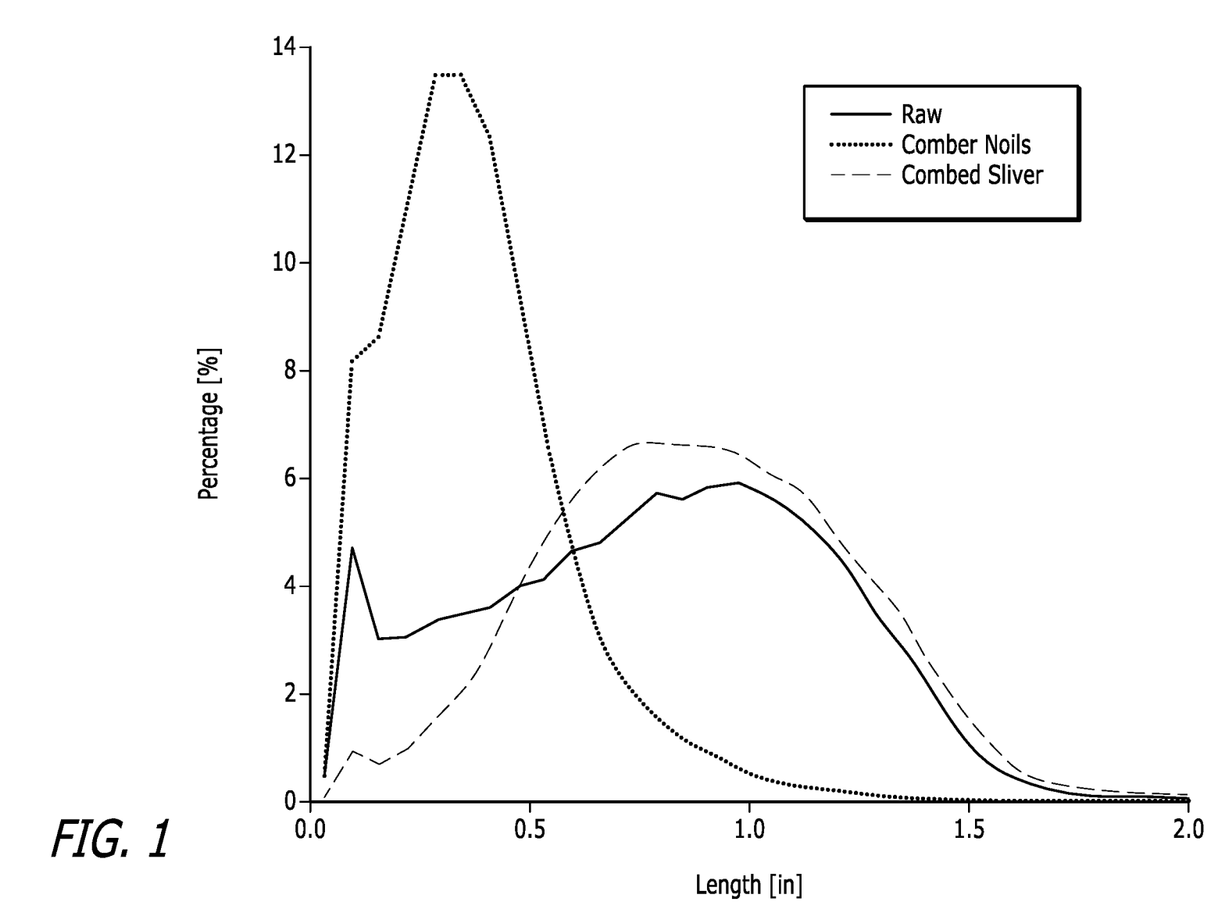
FIG. 1 depicts a graph showing improvements in sample distribution of fiber length achieved by combing.

If cotton could be adapted to airjet spinning, its throughput would make it competitive with rotor spinning (faster than rotor). It could produce yarns competitive with ring spun yarns in some market segments such as the 30Ne which is the main target market for U.S. cotton (the range of possible yarn counts is narrower than for ring spinning). However, because of a poor fiber length distribution when compared to man-made fibers, cotton is not the fiber of choice in the airjet spinning market. The current solution for this issue is to modify the distribution of fiber length with combing (see FIG. 1). While combing does result in an improved length distribution, it also lowers mill throughput and increases waste which results in lower profits for the spinning mills. New cultivars are needed which exhibit an improved within sample distribution of fiber length, competitive on international spinning markets.

The High Volume Instrument (HVI) is the primary method used to measure fiber length. HVI length parameters are based on the fibrograph method, where a beard of fibers is scanned with a light from base to tip, and the light attenuation through the beard is used to build a fibrogram curve. Currently, the HVI only reports two length parameters based on the fibrogram curve. The remaining information in the fibrogram curve is unused. However, this technology uses the complete curve when evaluating cotton fiber quality.

The other option is to use a slower instrument, such as the Advanced Fiber Information System (AFIS). This provides the complete within sample distribution in cotton fiber length. However, AFIS testing is too slow and expensive fir marketing and most breeding efforts.

Figure 2:
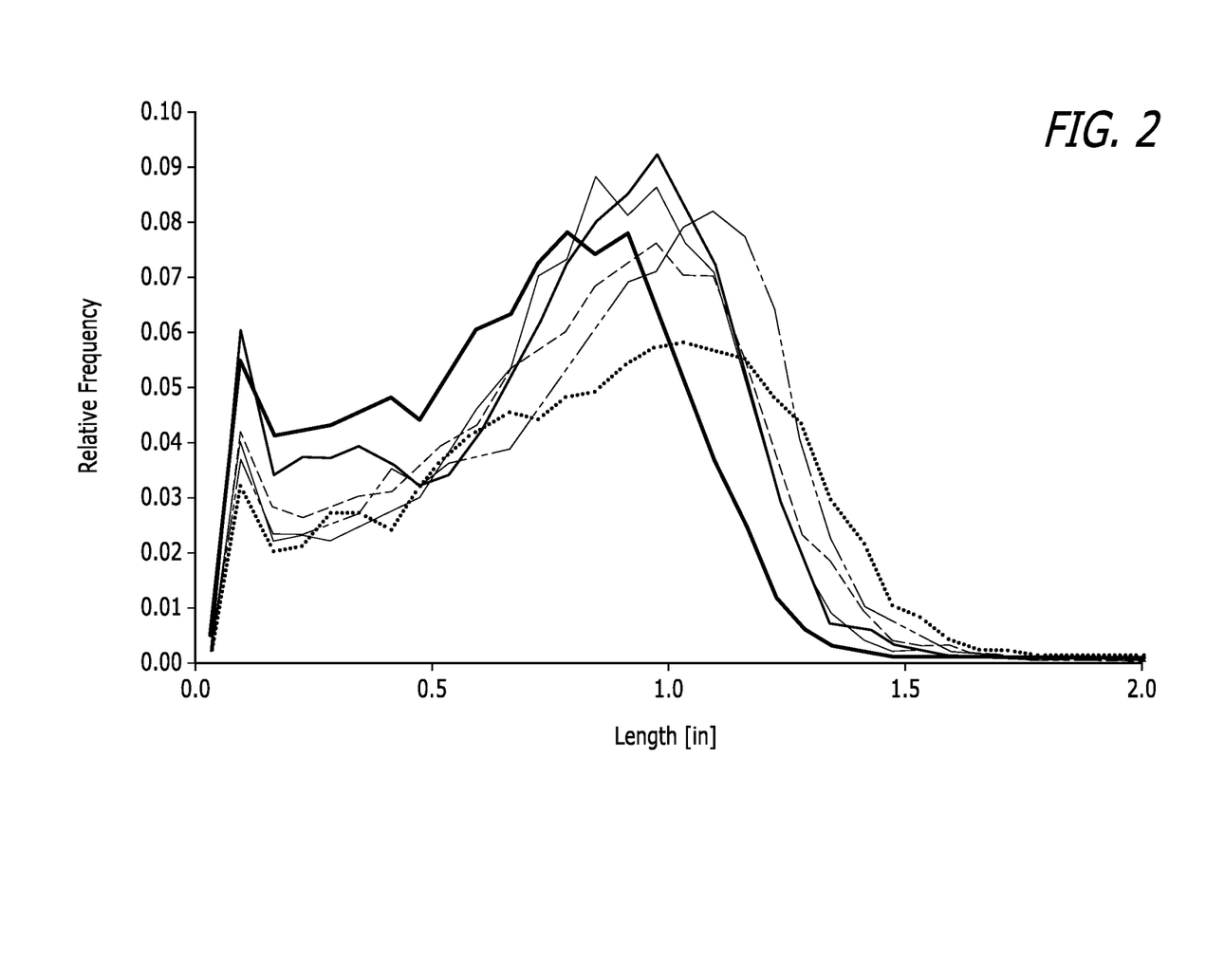
FIG. 2 depicts a graph showing variation in fiber length as measured by AFIS, despite having the same level of HVI Uniformity (81.3).

HVI testing is thus the primary tool used for evaluating fiber quality in germplasm development and cotton marketing. However, current HVI protocols, which provide Upper Half Mean Length (UHML) and Uniformity Index (UI), are unable to measure within sample variation in fiber length, information needed for predicting yarn quality for ring spinning and especially for airjet spinning (see FIG. 2).

Figure 3:
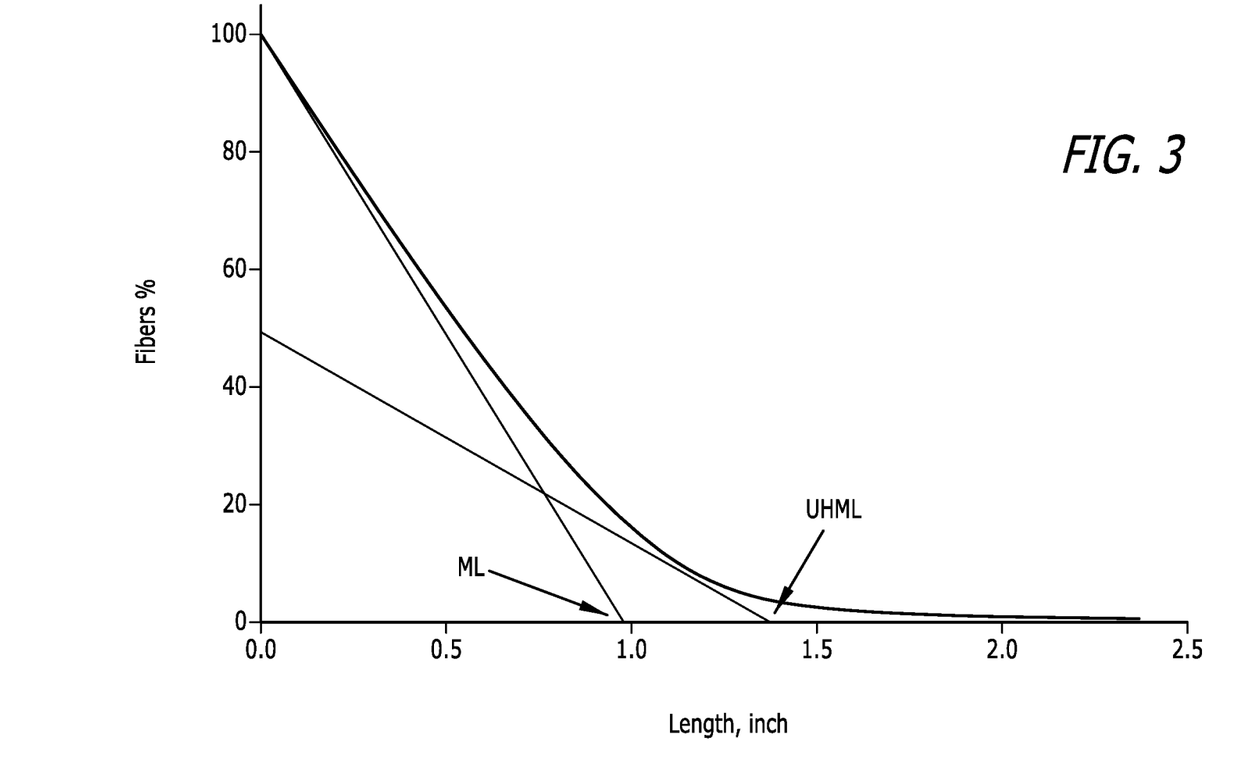
FIG. 3 depicts a typical fibrogram.
Figure 4:
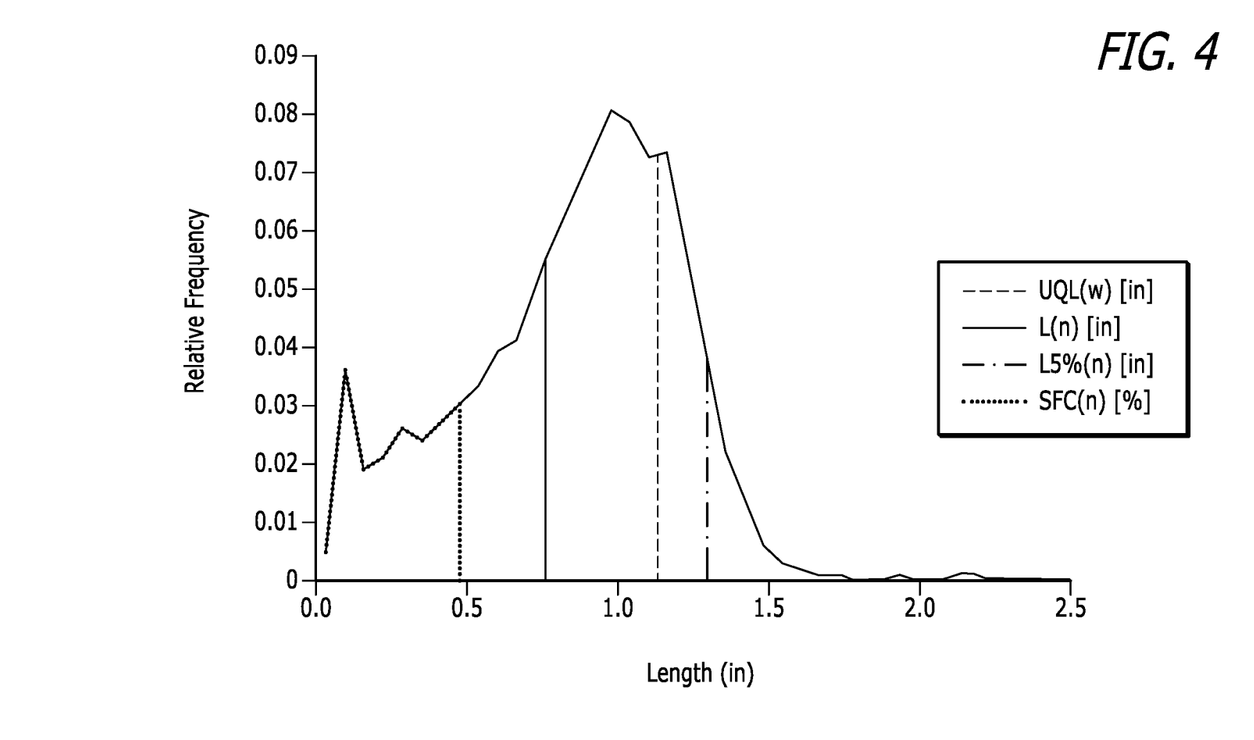
FIG. 4 depicts a chart showing a typical AFIS fiber length distribution by number.

While the standard HVI protocol only reports UHML and UI, the instrument may capture more information about within sample variation in fiber length that is currently unused (see FIG. 3). The fibrograph, the basis of HVI fiber length measurement, is an instrument that measures the light attenuation produced by scanning a sample of parallel fibers. The output of the optical system plotted as a function of distance is referred to as the fibrogram. In theory, the light attenuation is assumed to be related to the fiber mass between the lens. This assumption is questionable as current HVI systems use both the optical density and the micronaire to "measure" the weight of the sample being broken for the tensile test. Then, if it is assumed that fibers have uniform linear density or fineness, the measured amount is proportional to the number of fibers, Previous studies indicate that, within a sample, linear density is not independent of fiber length. Therefore, the second assumption is false. In conclusion, the current fibrogram provides length distribution information but it is not either a by weight or a by number distribution. In addition, currently, only Mean Length and Upper Half Mean Length are extracted from the fibrogram. These two measurements are highly collinear (Measure almost the same thing), and are calculated from the most distal portion of the fibrogram representing the tips of the longest fibers.

While imperfect, the length distribution by number from the Advanced Fiber Information System (AFIS) constitutes a standard, and its superiority as a predictor of yarn quality has been presented in the art via multiple research projects and publications.

In one embodiment of the present invention, the system retrieves the full fibrogram from the HVI. With the full fibrogram, the present invention is capable of extracting information from the fibrogram to better predict yarn quality than the standard HVI output. This additional information avoids testing breeding material with the AFIS, thus keeping testing cost about constant (compared with HVI testing only). While the HVI fiber length parameters are based on the fibrograph principle, and require the HVI to measure a fibrogram, the fibrogram curve measurement is not provided in a standard HVI report. It is therefore a preferred embodiment of the present invention to extract the HVI fibrogram and perform a statistical determination to extract all of the information available from the fibrogram. The information made available from the fibrogram was then compared with the AFIS length distribution and yarn quality parameters.

The HVI system operates out of several modes, two of which are relevant to these results. The first mode is System testing: This mode uses all components of the HVI system and provides the standard HVI report. The second mode is Length Module Testing: This mode only uses the length and strength testing module. Reports from t system can provide a fibrogram curve.

Figure 5:
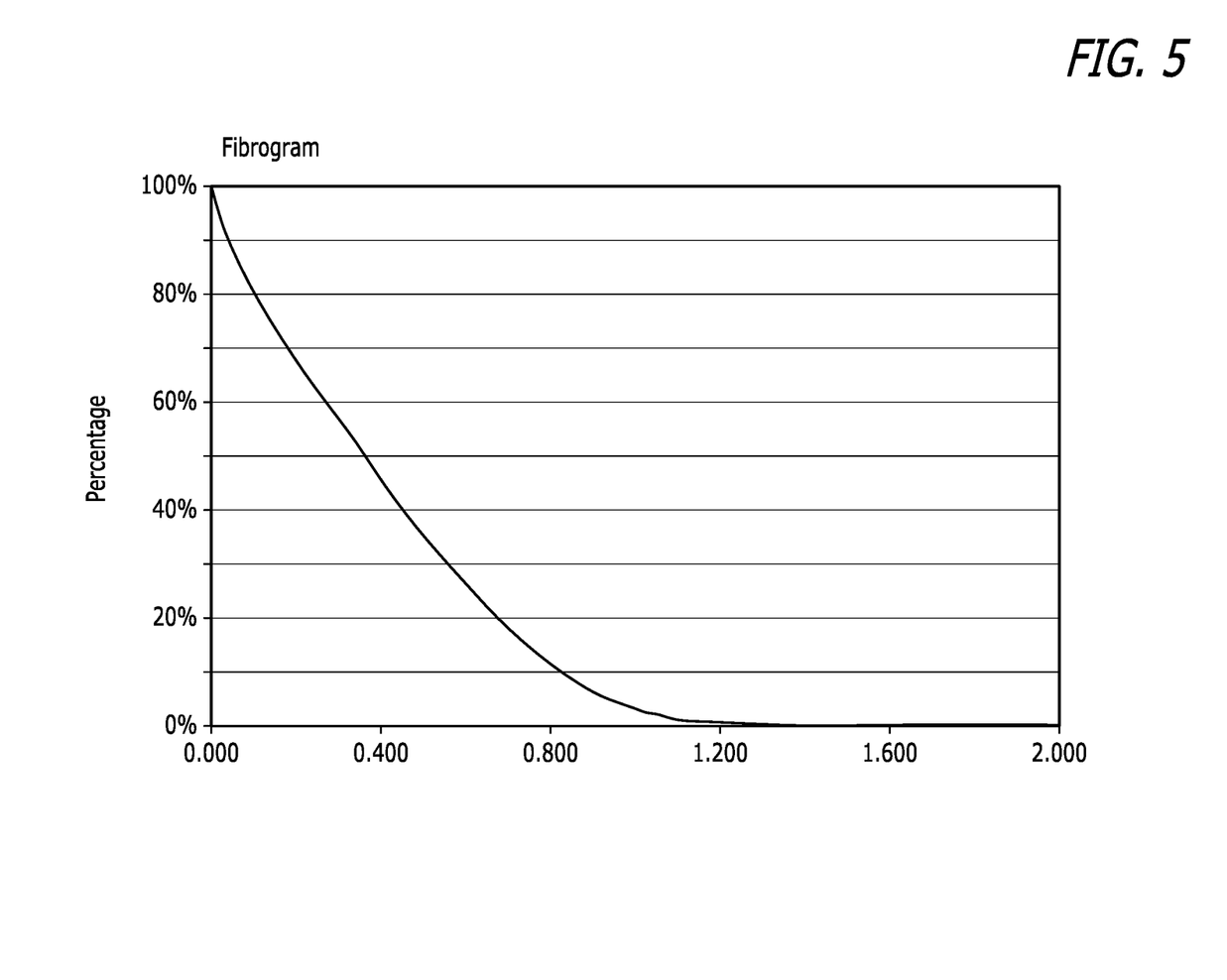
FIG. 5 depicts a standard vectored image of a fibrogram obtained from HVI module testing.
Figure 6:
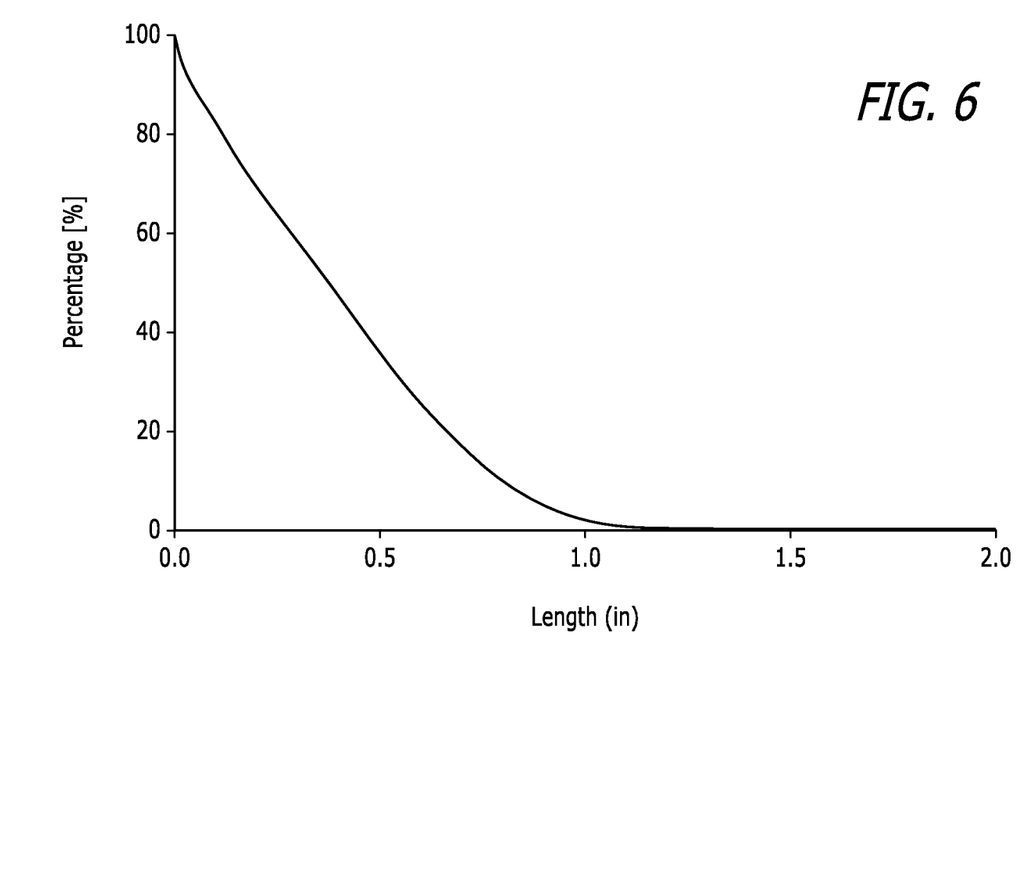
FIG. 6 depicts a fibrogram calculated from extracted vectored HVI data.

Length module testing is a nonstandard testing mode, and does not report to the central database in the Cotton Phenomics Laboratory (CPL). Thus, while a fibrogram is reported in Length Module Testing, it must be accessed through the native HVI software residing on the individual HVI systems. As a result, there is no report in the database that makes the fibrogram readily available for data analysis. The typical HVI module testing output provides a fibrogram report in several different graphical styles, but none with direct access to the raw data (see FIG. 5). In some of the length module reporting styles, the fibrogram image provided by the HVI length module testing report is vectored. This means the information used to generate the Fibrogram is embedded within the image file. Once the file format is convened to an open source format, the data can be extracted and manipulated directly (see FIG. 7). Manual extraction of the data is cumbersome and only a few samples can be converted at a time while connecting the data back to the original source. Thus, the automated system of the present invention is utilized to extract the needed data.

The fibrogram is generated, as light, attenuation, as scanned over a fiber beard. The starting point at the base of the scan is taken to be the point of 100% light attenuation, thus it is a standardized distribution. Fewer and fewer fibers extend to more distal points from the fibrograph comb. The fibrogram reaches 0% light attenuation after it scans past the most distal point of the beard, the tips of longest fibers in the samples.

The fibrogram itself is reported as a standardized optical amount plotted over 80 discrete fixed distance values. Length strength testing also provides the raw optical amount value, the true amount of light attenuation at the base of the beard, as "amount. The current HVI protocol measures variation in the fibrogram from only two points; the 1.8% span length for Upper Half Mean Length, and the 7.8% span length for the mean length. The Mean Length is not provided directly in the standard report, but is used in the calculation of the Uniformity Index. The Uniformity Index is calculated as the ratio of the Mean Length to the Upper Half Mean length, multiplied by 100. This calculation often requires the interpolation of data between two length bin values. Thus, the two most commonly used length parameters only characterize variation in length of the most distal tips of the longest fibers in the sample. The remainder of the fibrogram curve is currently unused.

The structure of the fibrogram limits its use in many standard statistical techniques. First, the fibrogram bins are highly collinear. i.e. The standardized optical amount in one bin is highly correlated to the standardized optical amount in the adjacent bin. Second, because the fibrogram is a standardized measurement, the value in any bin is bounded by 0 and 1. This may create some nonlinearity and instability when working with values near these extremes.

It is therefore an embodiment of the present invention to overcome such challenges using the following system: First, the total variation captured by a given set of fibrograms is captured using a distance matrix. The results provided herein are based on the Euclidean distance metric between fibrograms. Other distance metrics may also be used, such as chi-squared or bray Curtis distance. It may also be possible to express the total variation in the form of a covariance or correlation matrix, although that is not shown.

Once the total variation among, all samples is captured in matrix form, Eigen analysis is used to decompose the variation into the most basic components. This step may depend on the selected metric, or the goal of the analysis. Singular value decomposition may also be used. This step results in a vector of scores that represent each sample (fibrogram) in the new transformed space. These scores are the result of linear combinations of the total variation matrix. The first score represent the largest source of total variation among all fibrograms in the study. The second represents the second largest source, independent of the first, and so on. The decomposition also provides a vector which can be used to express the amount of the total variation captured by each score vector.

These scores provide a complete partitioning of the total multivariate space captured by the original fibrograms. Conveniently, each score characterizes an independent source of variation. With a prudent selection of a distance metric, the scores also characterize a linear multivariate space. Thus, the scores are used as a new set of variables that capture the total variation in the fibrogram curve among a set of samples. These variables can be used to characterize variation among samples, or relationships between variation in the fibrogram and other parameters of interest, such as yarn quality, other fiber quality parameters, or experimental factors.

The scores from the fibrogram are used as independent variables, and yam, quality parameters are used as dependent variables in a linear regression. The new set of variables (scores) contain all of the variation characterized in the original fibrograms. Some of this variation characterizes variation in fiber length, and some characterizes noise. Thus, the regression must be regularized so that improvements in each regression model come from the additional information in fiber length, and not noise. This is accomplished by regressing each yarn quality over the full set of Principal Coordinates Analysis (PCoA) scores using partial least square regression (PLSR), The PLSR can be based on any number of linear combinations of fibrogram scores. At least two parameters are typically extracted from the fibrogram, so at least two scores are used herein for exemplary purposes.

This step served the function of minimizing overfitting. There are 40 or so variables used to represent variation in the fibrograms. Each of these variables represents the light attenuation at a given distance along the scan of the fiber beard. It is not expected that all of the information captured by these 40 levels characterizes within sample variation in fiber length. Some variation in these measurements may be the result of random variation. PLSR was used to separate the within sample variation in fiber length from random variation in the fibrogram measurement. This was achieved by first relating the variation in the fibrogram directly to variation in yarns quality and extracting either the first two or three, scores in this relationship. Thus, if 2 scores are extracted, these are 2 independent variables that characterize within sample variation in fiber length from the fibrogram with the best relationship to that yarn quality.

Distance Based (2 score) set—2 scores for one model, because HVI already reports 2 variables. This makes these two models have the same number of parameters, Distance Based (3 score) set—3 scores were used in a different set, because it has been determined a fibrogram may have at least 3 variables worth of information.

These are referred to as the "PLSR Scores". These PLSR scores were used as length parameters predictors in a set of linear models of yarn quality. Some yarn qualities were square root transformed, indicated by an "x". A second set of Partial Least Square regression equations were used with the raw HVI fibrograms used directly as the independent variables. This is referred to as the raw fibrogram of the present invention.

Figure 7:
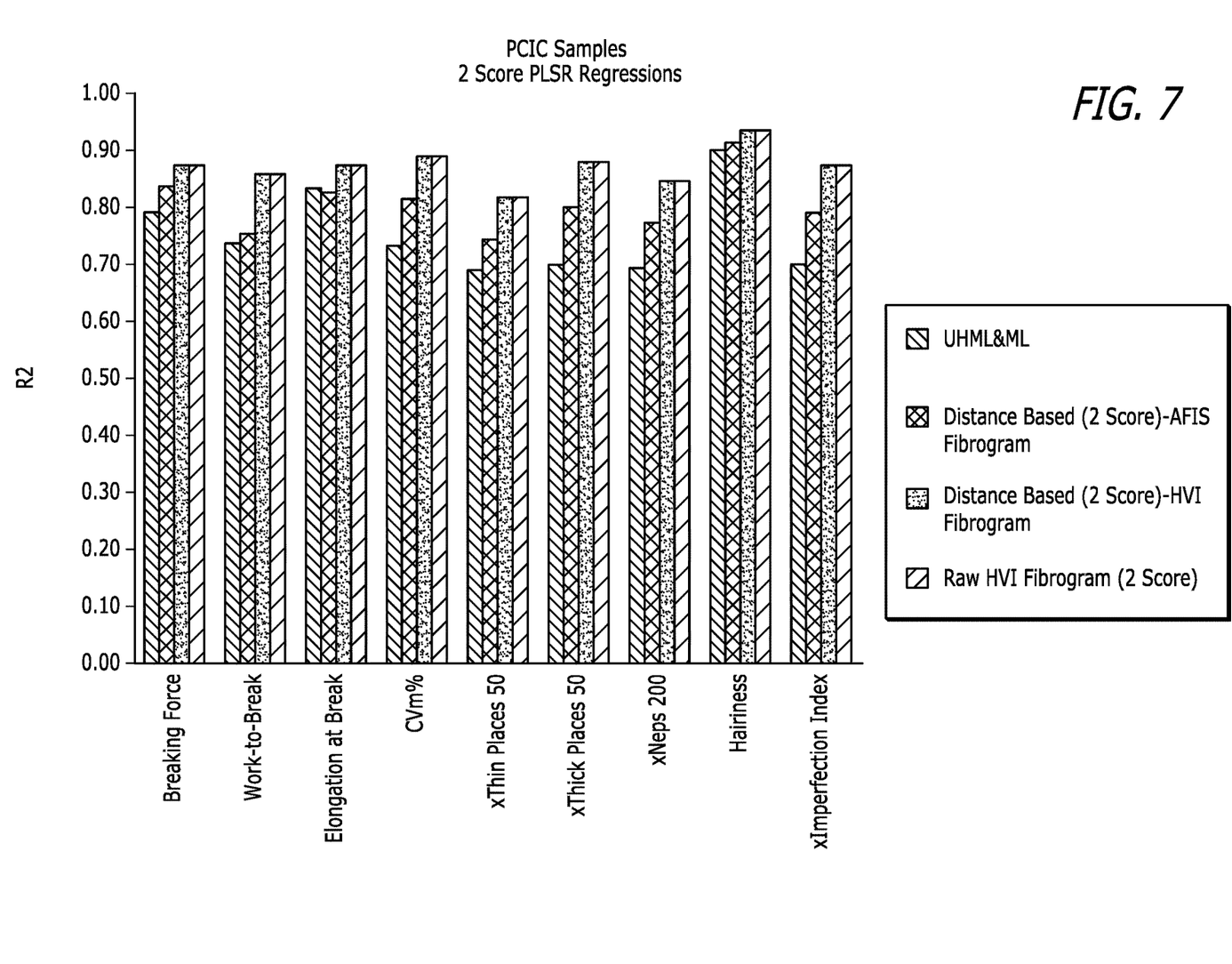
FIG. 7 depicts a chart showing a 2-score PLSR regression for commercial-like samples.

The results of this illustrative analysis for two separate samples, a commercial sample (PCIC) and a breeder sample (Smith) are summarized in the FIGS. 7-11. The system of the present invention was utilized to measure fibrograms for two very different types of cotton fiber samples, a set of commercial bales and a set of breeder samples. Fiber from these samples was also spun into yarn. The additional information retrieved from the fibrogram using this technology explained a greater amount of variation in spun yarn quality than traditional HVI parameters, or the AFIS fiber length distribution. Using the full fibrogram as developed by the system of the present invention consistently outperforms the standard HVI parameters when explaining variation in yarn quality. Turning to FIG. 7, PCIC Samples were analyzed with various systems, and 2 score PLSR is provided for the various techniques, including: (1) UHML and ML; (2) Distance Based (2 score) ARS Fibrogram; (3) Distance Based (2 score) HVI Fibrogram; and (4) Raw HVI Fibrogram (2 score). Analysis included various Motors including, Breaking Force, Work-York-to-Break, Elongation At Break, CVm %, square root transformed Thin Places 50, square root transformed Thick Places 50, square root transformed Neps 200, Hairiness, and square root transformed Imperfection index, all of which explain variation in yarn quality.

One goal of breeding is to develop germplasm with the potential to produce fiber that is competitive as a raw material on the prevailing spinning markets. The current market is focused on ring spinning. These results demonstrate that the present invention provides important information about the within-sample distribution of fiber length needed for characterizing the quality of yarns that could be spun with the fiber produced from their germplasm. This further enables a breeder to make more informed decisions about selections in germplasm development Indeed, the present invention helps breeders develop varieties that produce fiber with a length distribution that is more efficient to process and results in higher quality yarns. Other researchers can use additional data provided by this invention to evaluate varieties and agronomic practices that result in a more ideal within sample distribution of fiber length, thus allowing producers to sell their products into higher value markets, increasing their income. Spinning mills select bales from their warehouse and blend them together as a part of the spinning process. The present invention allows spinning mills to target yarn manufacturing goals. Thus, the present invention could be used by mills to manage their blends and spinning equipment settings.

Figure 8:
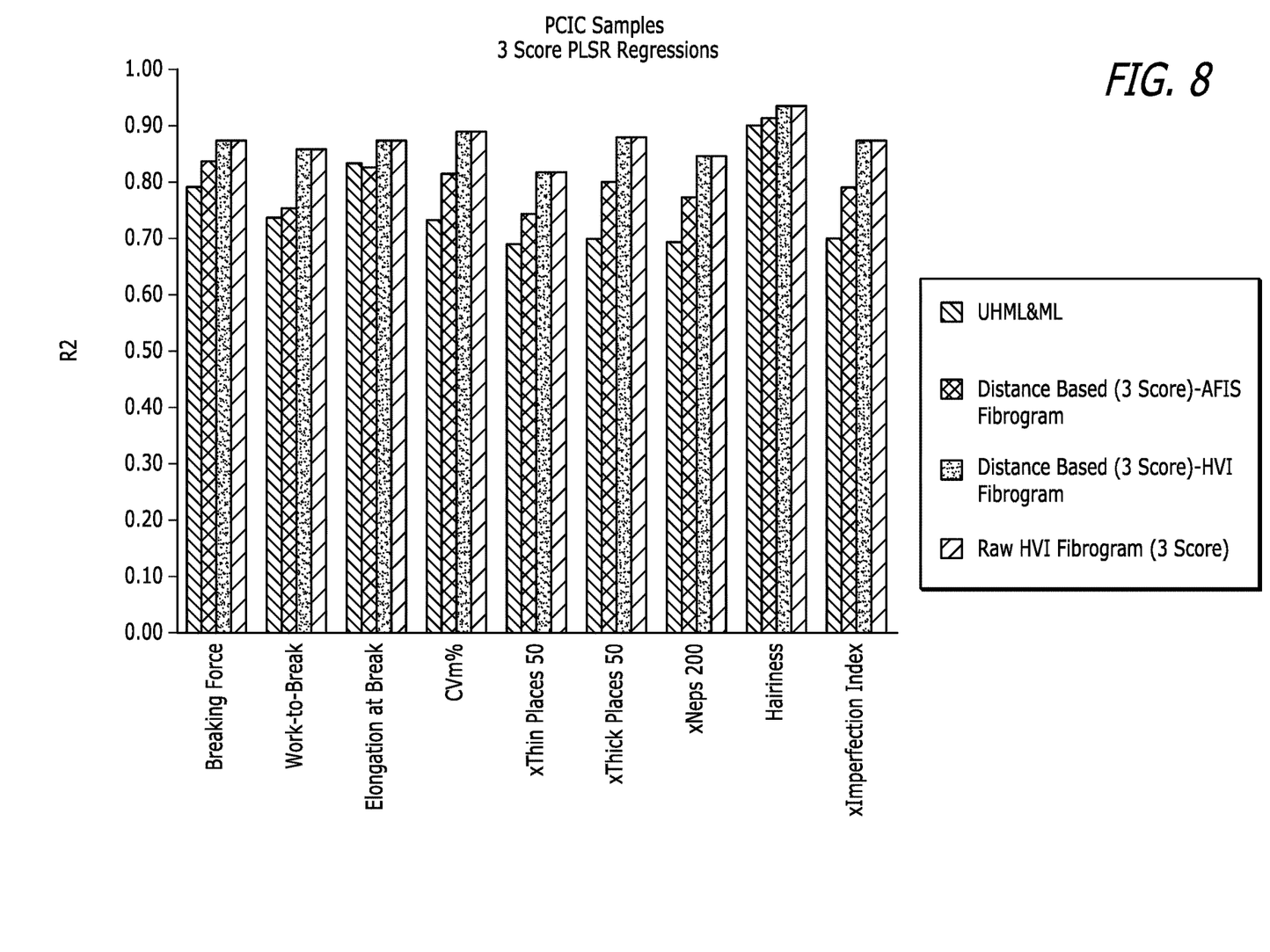
FIG. 8 depicts a chart showing a 3-score PLSR regression for commercial-like samples.
Figure 9:
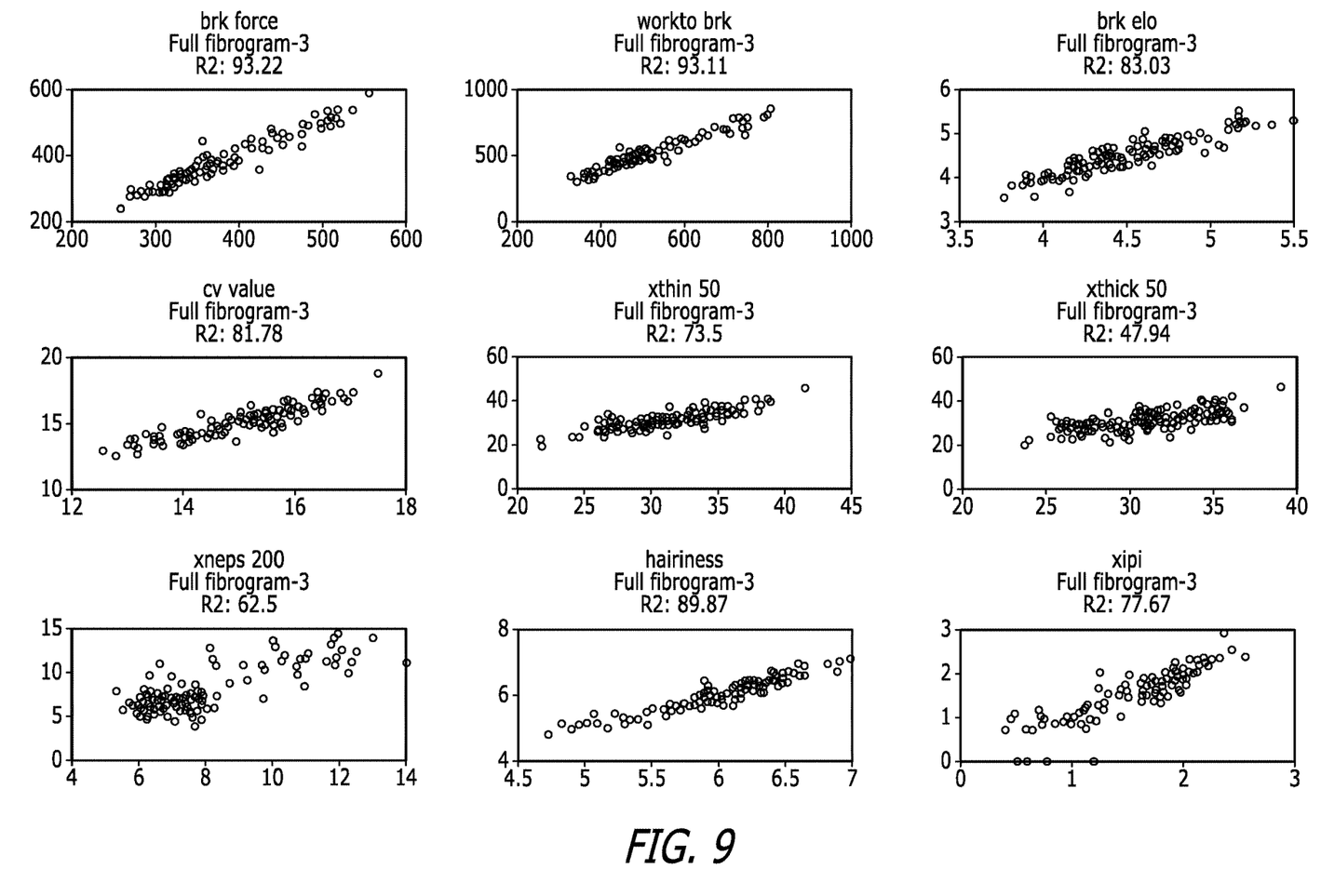
FIGS. 9A-I depict scatterplots for yarn quality models using 3 distance based scores along with the standard non-length HVI fiber quality parameters.

FIG. 8 presents PCIC Samples and 3 score PLSR results using various systems including: (1) UHML and ML; (2) Distance Based (3 score) AFIS Fibrogram, (3) Distance Based (3 score) HVI Fibrogram; and (4) Raw HVI Fibrogram (3 score). Analysis included various factors including, Breaking Force, Work-to-Break, Elongation At Break, CVm %, square root transformed Thin Places 50, square root transformed Thick Places 50, square root transformed Neps 200, Hairiness, and square root transformed Imperfection Index, which collectively explain variation in yarn quality FIG. 9 presents scatterplots for yarn quality models using three (3) distance based scores along with the standard non-length HVI fiber quality parameters: Breaking force (brk force), Work-to-break (workto brk), Elongation at break (brk elo), CVm % (cv value), square root transformed Thin places 50 (xthin 50), square root transformed Thick places 50 (xthick 50), square root transformed Neps 200 (xneps 200), Hairiness (hairiness), and square root transformed Imperfection index (xipi).

Figure 10:
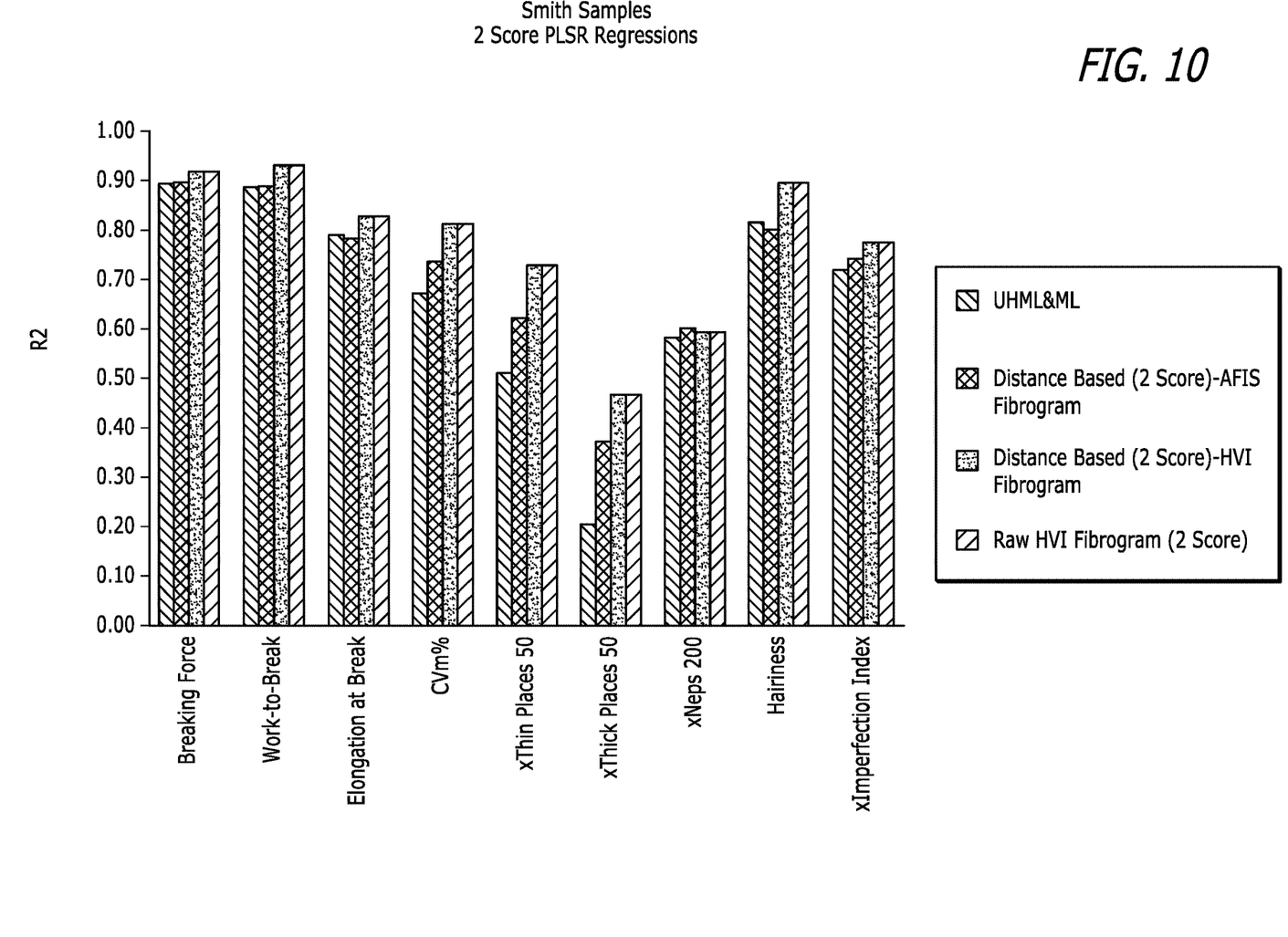
FIG. 10 depicts a chart showing 2-score PLSR regression for breeder samples.
Figure 11:
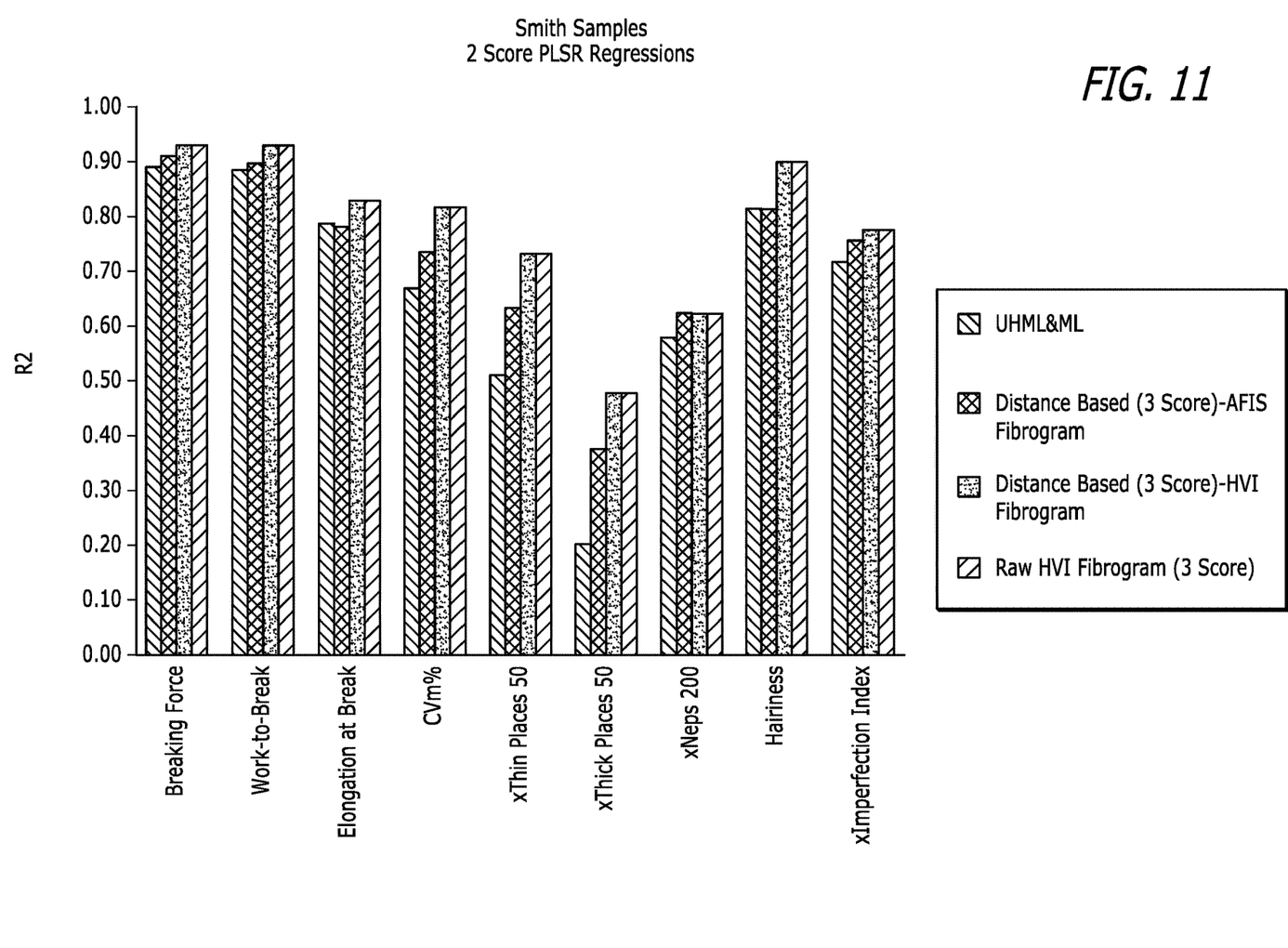
FIG. 11 depicts a chart showing 3-score PLSR regression for commercial like samples.

FIG. 10 provides 2 score PLSR results of Smith samples, including: (1) LTHML and ML; (2) Distance Based (2 score) AEIS Fibrogram; (3) Distance Based (2 score) HVI Fibrogram; and (4) Raw HVI Fibrogram (2 score). Results are shown in FIG. 10 for various factors including, Breaking Force, Work-to-Break, Elongation At Break, CVm %, square root transformed Thin Places 50, square root transformed Thick Places 50, square root transformed Neps 200, Hairiness, and square root transformed Imperfection Index, which collectively explain variation in yarn quality.

FIG. 8 presents Smith Samples and 3 score PLSR results using various systems, including: (1) UHML and ML; (2) Distance Based (3 score) APIS Fibrogram; (3) Distance Based (3 score) HVI Fibrogram; and (4) Raw HVI Fibrogram (3 score). Analysis included various factors including, Breaking Force, Work-to-Break, Elongation At Break, CVm %, square root transformed Thin Places 50, square root transformed Thick Places 50, square root transformed Neps 200, Hairiness, and square root transformed Imperfection Index, which collectively explain variation in yarn quality.

The system and method of the present invention, in one embodiment, further includes a general-purpose computing device in the form of a computer. The components of the computer can include, but are not limited to, one or more processors or processing units, a system memory, and a system bus that couples various system components including the processor to the system memory. The computer may be, for example, a desktop computer or a portable device computer, such as a cellular telephone, a smart phone, a display pager, a radio frequency (RF) device, an infrared (IR) device an Near Field Communication (NFC) device, a Personal Digital Assistant (PDA), a handheld computer, a tablet computer, a laptop computer, phablets, a wearable computer, an integrated device combining various features, such as features of the forgoing devices, or the like.

The system bus represents one or more of several possible types of bus structures, including a memory bus or memory controller, a peripheral bus, an accelerated graphics port, and a processor or local bus using any of a variety of bus architectures. By way of example, such architectures can include an Industry Standard Architecture (ISA) bus, a Micro Channel Architecture (MCA) bus, an Enhanced ISA (EISA) bus, a Video Electronics Standards Association (VESA) local bus, and a Peripheral Component Interconnects (PCI) bus also known as a Mezzanine bus. This bus, and all buses specified in this description can also be implemented over a wired or wireless network connection, collectively a network. The bus, and all buses specified in this description can also be implemented over a wired or wireless network connection and each of the subsystems, including the processor, a mass storage device, an operating system, an image construction software, a nanoparticle movement image construction software, light signal data, the system memory, an OCT input interface, an OCT output interface, a display adapter, a display device, a human interface device, and a digital image capture device, can be contained within one or more remote computers at physically separate locations, connected through buses of this form, and via a network, in effect implementing a fully distributed system.

The computer can include a variety of computer readable media. Such media can be any available media that is accessible by the computer and includes both volatile and non-volatile media, removable and non-removable media.

The system memory includes computer readable media in the form of volatile memory, such as random access memory (RAM), and/or non-volatile memory, such as read only memory (ROM). The system memory typically contains data such as light signal data and/or program modules such as operating system, image construction software and nanoparticle movement for cellular membrane tension level or intenial strain field change) image construction software that are immediately accessible to and/or are presently operated on by the processing unit.

The computer can also include other removable/non-removable, volatile/non-volatile computer storage media, such as a mass storage device which can provide non-volatile storage of computer code, computer readable instructions, data structures, program modules, and other data for the computer. For example, a mass storage device can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

In one exemplary embodiment, a subsample of fiber from a set of bales is evaluated on the HVI. A fibrogram curve is generated from each of these samples. In a raw form, the fibrogram curve represents the length variation for each sample as a vector of 81 variables, in the current HVI system, two measurements are extracted, the Upper Half Mean Length and the Mean Length, and the curve is discarded. These two measurements are taken from the same region of the fibrogram, the region representing the longest fibers, and as a result, these two measurements are inadequate for two reasons. The parameters do not characterize the complete within sample variation in fiber length captured by the fibrogram, and the parameters are highly collinear. The parameters are collinear enough that they could be considered as characterizing the same variation in fiber length (i.e. They are effectively one variable).

In the present invention, rather than extracting to length parameters from the extreme points of the curve or another isolated pan of the fibrogram, all of the information available is characterized. The embodiments of the present invention accomplish this by applying multidimensional scaling to the complete set of raw fibrogram curves, producing a set of loading vectors and a set of scores. The complete set of scores provides a summary of the total variation captured by the fibrogram, with each score representing an independent type of variation characterized by the fibrogram. Mathematically, there can be as many scores as there are values reported in the fibrogram vector. There are fewer in practice. For example, some regions of the fibrogram do not capture variation in fiber length because the fibrogram includes the regions where fibers in the beard do not extend. However, results from commercial and breeder samples show that at least three of these scores characterize variation in fiber length that explains variation in yarn quality. This is important information for researchers, such as breeders, and the remainder of the cotton industry. The present invention provides a novel system beyond the current art, as current HVI protocols provide at most two length parameters characterizing an isolated region of the fibrogram curve. The present invention provides at least three length parameters that each characterize an independent type of variation in fiber length.

In summary, the present invention represents a system and method for determining fiber yarn quality by developing a full fibrogram curve from an HVI, thus providing information about cotton fiber quality that is needed for explaining variation in processing performance and yarn quality, while using the most common fiber quality evaluation instrument, the HVI. This information is needed to develop and market new varieties that meet the demands of international spinning markets without relying on slower and more expensive techniques, such as AFIS. The system and method of the present invention may be performed by a computer upon determining the HVI curve via HVI analysis.

Those skilled in the art will recognize that the methods and systems of the present invention may be implemented in many manners and as such are not to be limited by the foregoing exemplary embodiments and examples. In other words, functional elements being performed by single or multiple components, in various combinations of hardware and software or firmware, and individual functions, may be distributed among various software applications at either the client level or server level or both. In this regard, any number of the features of the different embodiments described herein may be combined into single or multiple embodiments, and alternate embodiments having fewer than, or more than, all of the features described herein are possible.

Functionality may also be, in whole or in part, distributed among multiple components, in manners now known or to become known. Thus, myriad combinations are possible in achieving the functions, features, and preferences described herein. Moreover, the scope of the present invention covers conventionally known manners for carrying out the described features as well as those variations and modifications that may be made to the processes, composition, or compounds described herein as would be understood by those skilled in the art now and hereafter.

Furthermore, the embodiments of methods presented and described as diagrams, schematics or flowcharts in this disclosure (such as the Figures) are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure.

What is claimed is:

1. A system for estimating unknown fiber quality of a fiber sample, comprising:
   a. a high volume instrument (HVI) for collecting a respective set of fiber samples from the HVI and representing the respective set of fiber samples as a fibrogram having a distance matrix; and b. a computer for:
   i. decomposing a total variation captured in said distance matrix to form a matrix of transformed fibrogram data, said matrix of transformed fibrogram data comprising a vector of scores to represent each sample;
   ii. mutually exclusively partitioning a total multivariate space captured by the initial fibrograms into a set of independent variables from the HVI; and
   iii. explaining variation in yarn quality by regressing each yarn quality parameter over said vector of scores obtained from the matrix of transformed fibrogram data.

2. The system of claim 1, wherein the distance matrix is based on the Euclidean distance metric between initial fibrograms.

3. The system of claim 1, wherein the distance matrix is based on the chi-squared distance metric between initial fibrograms.

4. The system of claim 1, wherein the distance matrix is based on the Bray-Curtis dissimilarity metric between initial fibrograms.

5. The system of claim 1, wherein the distance matrix is based on a correlation matrix between initial fibrograms.

6. The system of claim 1, wherein the decomposition may comprise singular value decomposition.

7. The system of claim 1, wherein the vector of scores further comprises at least one score representing the largest source of total variation among all initial fibrograms.

8. The system of claim 1, wherein the vector of scores further comprises at least two scores representing a first score representing the largest source of total variation among all initial fibrograms, and a second score representing the second largest source of total variation among all initial fibrograms.

9. A method of estimating unknown fiber quality of a fiber sample, comprising:
   a. collecting a respective set of initial fibrograms comprising a set of fiber samples from a high volume instrument (HVI) and representing the set of fiber samples as a distance matrix;
   b. decomposing a total variation captured in said matrix form from the distance matrix to form a matrix of transformed fibrogram data, said subsequent matrix of transformed fibrogram data comprising a vector of scores to represent each sample;
   c. mutually exclusively partitioning a total multivariate space captured by the initial fibrograms into a set of independent variables from the HVI; and
   d. explaining variation in yarn quality by regressing each yarn quality parameter over said vector of scores obtained from the transformed fibrogram data.

10. The method of claim 9, wherein the distance matrix is based on the Euclidean distance metric between initial fibrograms.

11. The method of claim 9, wherein the distance matrix is based on the chi-squared distance metric between initial fibrograms.

12. The method of claim 9, wherein the distance matrix is based on the Bray-Curtis dissimilarity metric between initial fibrograms.

13. The method of claim 9, wherein the distance matrix is based on a correlation matrix between initial fibrograms.

14. The method of claim 9, wherein the decomposition may comprise singular value decomposition.

15. The method of claim 9, wherein the vector of scores further comprises at least one score representing the largest source of total variation among all initial fibrograms.

16. The method of claim 9, wherein the vector of scores further comprises at least two scores representing a first score representing the largest source of total variation among all initial fibrograms, and a second score representing the second largest source of total variation among all initial fibrograms.

17. The method of claim 9, wherein the vector of scores further comprises more than two scores representing ranked scores representing the source of total variation among all initial fibrograms from largest to smallest.

18. The method of claim 9, wherein the fiber quality further comprises quality parameters selected from a group consisting of: breaking force, work-to-break, elongation at break, yarn irregularity (CVm %), thin places, thick places, neps, hairiness, imperfection index, and combinations thereof.

19. The method of claim 9, further comprising performing said determining each fiber quality parameter on a computer.

20. The method of claim 9, wherein the vector of scores further comprises more than two scores representing ranked scores representing the source of total variation among all initial fibrograms from largest to smallest.

21. The method of claim 9, wherein the fiber quality further comprises quality parameters selected from a group consisting of: breaking force, work-to-break, elongation at break, yarn irregularity (CVm %), thin places, thick places, neps, hairiness, imperfection index, and combinations thereof.

* * * * *